United States Patent
Pickenäcker et al.

(10) Patent No.: US 8,163,139 B2
(45) Date of Patent: Apr. 24, 2012

(54) PROCESS FOR THE DISTILLATIVE SEPARATION OF MIXTURES COMPRISING MONOETHYLENE GLYCOL AND DIETHYLENTRIAMINE

(75) Inventors: Karin Pickenäcker, Lampertheim (DE); Johann-Peter Melder, Böhl-Iggelheim (DE); Bram Willem Hoffer, Heidelberg (DE); Thomas Krug, Worms (DE); Gunther van Cauwenberge, Temse (BE); Frank-Friedrich Pape, Kleinniedesheim (DE)

(73) Assignee: BASF SE (DE)

( * ) Notice: Subject to any disclaimer, the term of this patent is extended or adjusted under 35 U.S.C. 154(b) by 898 days.

(21) Appl. No.: 12/279,372

(22) PCT Filed: Feb. 8, 2007

(86) PCT No.: PCT/EP2007/051227
§ 371 (c)(1),
(2), (4) Date: Aug. 14, 2008

(87) PCT Pub. No.: WO2007/093555
PCT Pub. Date: Aug. 23, 2007

(65) Prior Publication Data
US 2009/0065346 A1 Mar. 12, 2009

(30) Foreign Application Priority Data
Feb. 14, 2006 (EP) .................... 06101641

(51) Int. Cl.
*B01D 3/34* (2006.01)
*B01D 3/00* (2006.01)
(52) U.S. Cl. ............. 203/64; 203/28; 203/63; 203/71
(58) Field of Classification Search .......... 203/59, 203/64, 63; 210/634; 564/498, 499
See application file for complete search history.

(56) References Cited

U.S. PATENT DOCUMENTS

| 3,038,904 | A | * | 6/1962 | Godfrey | 544/225 |
| 3,055,809 | A | * | 9/1962 | Lichtenwalter | 203/14 |
| 3,433,788 | A | * | 3/1969 | Hawkes et al. | 544/106 |
| 4,014,933 | A | * | 3/1977 | Boettger et al. | 564/447 |
| 4,552,957 | A | * | 11/1985 | McEntire | 544/177 |
| 4,855,505 | A | | 8/1989 | Köll | |
| 2007/0043217 | A1 | | 2/2007 | Siegert et al. | |

FOREIGN PATENT DOCUMENTS

DE 217509 A1 1/1985
WO WO-2005/037769 A1 4/2005

OTHER PUBLICATIONS

C.M. Barnes, et al., "Ethylenediamine by Low-Pressure Ammonolysis of Monoethanolamine," *Ind. Eng. Chem. Prod. Res. Dev.*, (1981), pp. 399-407, vol. 20.
M. Arné, "Alkyl Amines," *Process Economics Program*, (Mar. 1981), pp. 7, 8 13-16, 43-107, 113, 117, Report No. 138, SRI International, Menlo, Park, CA.
L. Fu-Ming, "Extractive Distillation: Close-Boiling Point," *Chemical Engineering*, (Nov. 1998), pp. 112-116, 118, 120, vol. 12.

* cited by examiner

*Primary Examiner* — Duane Smith
*Assistant Examiner* — Patrick McCarty
(74) *Attorney, Agent, or Firm* — Connolly Bove Lodge & Hutz LLP

(57) ABSTRACT

Processes comprising: providing a mixture comprising monoethylene glycol and diethylenetriamine; and subjecting the mixture to extractive distillation with a diethylenetriamine-selective solvent comprising triethylene glycol to provide a first stream comprising monoethylene glycol and a second stream comprising diethylenetriamine; wherein the first stream is substantially free of diethylenetriamine, and wherein the second stream is substantially free of monoethylene glycol.

13 Claims, 1 Drawing Sheet

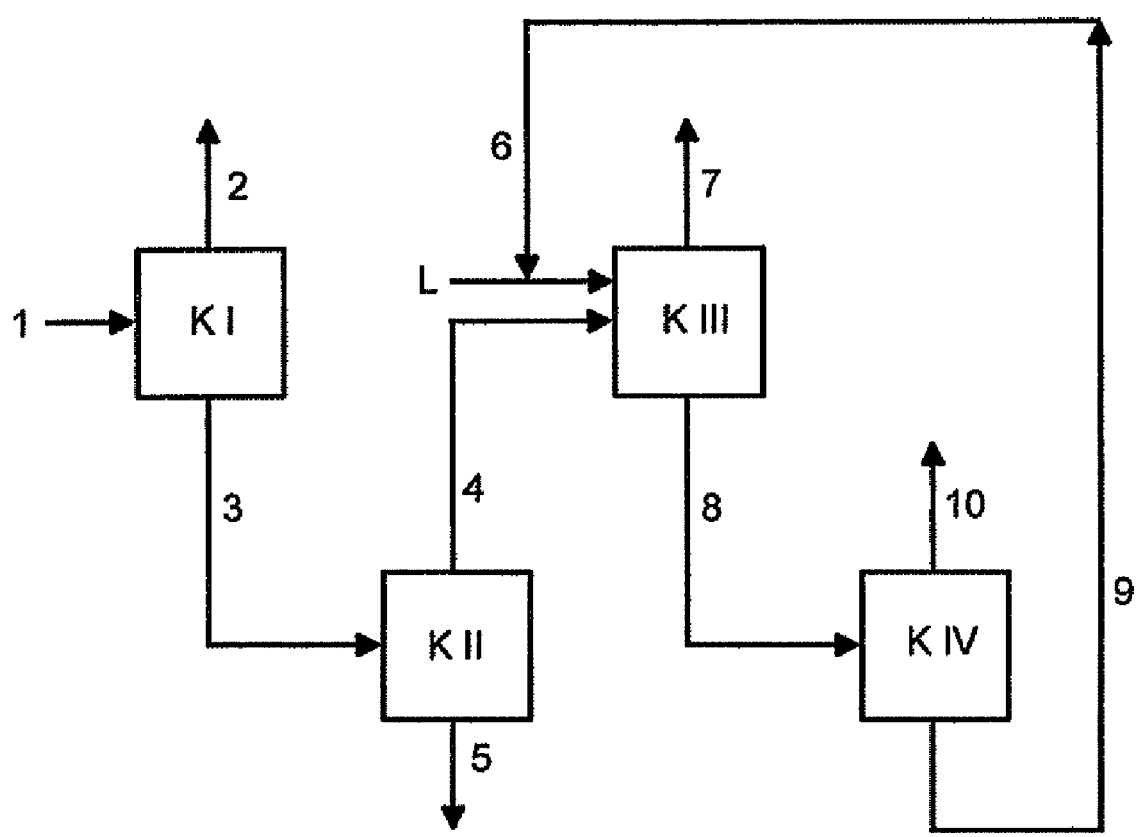

US 8,163,139 B2

PROCESS FOR THE DISTILLATIVE SEPARATION OF MIXTURES COMPRISING MONOETHYLENE GLYCOL AND DIETHYLENTRIAMINE

CROSS-REFERENCE TO RELATED APPLICATIONS

This application is a national stage application, under 35 U.S.C. §371, of PCT/EP2007/051227, filed Feb. 8, 2007, which claims priority of European Patent Application No. 06101641.6, filed Feb. 14, 2006.

BACKGROUND OF THE INVENTION

Mixtures comprising monoethylene glycol and diethylenetriamine are obtained, for example, in the process for preparing ethyleneamines and ethanolamines by hydrogenating amination of monoethylene glycol (hereinafter: MEG) in the presence of a catalyst.

In known processes, a mixture of ethanolamines and ethyleneamines is generally obtained; among these, especially ethylenediamine (hereinafter: EDA) and diethylenetriamine (bis(2-aminoethyl)amine; hereinafter: DETA) are important valuable substances whose uses include use as solvents, stabilizers, for synthesis of chelating agents, synthetic resins, medicaments, inhibitors and interface-active substances.

EDA is used in particular as a raw material for fungicides and insecticides,

DETA finds use in particular as a solvent for dyes and is a starting material for preparing ion exchangers, pesticides, antioxidants, corrosion protectants, complexing agents, textile assistants and absorbents for (acidic) gases.

Nonlinear amines in the product mixture of the ethyleneamines and ethanolamines and especially cyclic amines, predominantly piperazine and piperazine derivatives, are, in contrast, less valued to unwanted.

For the preparation of ethyleneamines, numerous processes are described in the literature.

According to PEP Report No. 138, "Alkyl Amines", SRI International, 03/1981, in particular pages 7, 8 13-16, 43-107, 113, 117, the reaction of dichloroethane with ammonia at molar ratios of 1:15 affords DETA with a proportion of the ethyleneamines formed of greater than 20% by weight. In addition to 40% by weight of EDA, however, 40% by weight of higher ethyleneamines are obtained.

Amination of monoethanolamine (hereinafter: MEOA) with ammonia (cf., for example, the abovementioned PEP Report, U.S. Pat. No. 4,014,933 (BASF AG)) allows the formation of these higher ethyleneamines (i.e. ethyleneamines having a boiling point above that of triethylenetetramine (hereinafter: TETA)) to be substantially suppressed in favor of EDA. However, the by-products obtained in this reaction are aminoethylethanolamine (hereinafter: AEEA) and piperazine (hereinafter: PIP).

Ind. Eng. Chem. Prod. Res. Dev. 1981, 20, pages 399-407, (C. M. Barnes et al.) describes the ammonolysis of MEOA to EDA over nickel catalysts on an $SiO_2$—$Al_2O_3$ mixed support. Addition of water and the powdered catalyst were purportedly advantageous in increasing the yield of EDA.

U.S. Pat. No. 4,855,505 discloses a process for hydroaminating monoethylene glycol for example with ammonia for example in the presence of a catalyst which comprises from 4 to 40% by weight of nickel or cobalt and from 0.1 to 5% by weight of ruthenium which has been introduced as a solution of a ruthenium halide on a porous metal oxide support comprising at least 50% by weight of activated alumina. The catalyst is used, by way of example, in the form of tablets having a length and a diameter of about 3 mm.

The product streams obtained in the processes described are separated by distillation to obtain the individual products in pure form, in particular the particularly desired EDA and DETA. A problem here is that MEG and DETA form an azeotrope which is virtually independent of the pressure and therefore cannot be separated by pressure swing distillation. The azeotropic composition is approx. 44% by weight of MEG and 56% by weight of DETA and has a boiling point at 150 mbar of 154° C., compared to the boiling point of pure MEG of 144° C. and of pure DETA of 142° C., in each case at the pressure stated above of 150 mbar.

BRIEF SUMMARY OF THE INVENTION

The invention relates to a process for distillatively separating mixtures comprising monoethylene glycol and diethylenetriamine.

It was accordingly an object of the invention to provide a process by which MEG and DETA can be removed by distillation from mixtures comprising them.

The solution consists in a process for distillatively separating a mixture comprising monoethylene glycol and diethylenetriamine into a stream which comprises monoethylene glycol and is substantially free of diethylenetriamine, and a stream which comprises diethylenetriamine and is substantially free of monoethylene glycol, which comprises performing the separation by extractive distillation with triethylene glycol as a selective solvent for diethylenetriamine.

It has been found that, surprisingly, triethylene glycol (hereinafter TEG) is outstandingly suitable as a selective solvent for the preparation of MEG and DETA by extractive distillation.

In particular, use of TEG as a selective solvent for DETA allows a mixture comprising MEG and DETA to be separated into a stream which comprises MEG and whose proportion of DETA is less than 5% by weight, preferably less than 0.1% by weight, more preferably less than 10 ppm, and into a stream which comprises DETA and whose proportion of MEG is less than 2% by weight preferably less than 0.1% by weight, more preferably less than 10 ppm.

BRIEF DESCRIPTION OF THE SEVERAL VIEWS OF THE DRAWING

The foregoing summary, as well as the following detailed description of the invention, may be better understood when read in conjunction with the appended drawings. For the purpose of assisting in the explanation of the invention, there are shown in the drawings representative embodiments which are considered illustrative. It should be understood, however, that the invention is not limited in any manner to the precise arrangements and instrumentalities shown.

In the drawings:

FIG. 1 is schematic diagram of a process according to one embodiment of the present invention.

DETAILED DESCRIPTION OF THE INVENTION

In an advantageous process variant, the mixture comprising MEG and DETA is obtained from the reaction mixture of the hydrogenating amination of MEG with ammonia in the presence of a heterogeneous catalyst, from which lower- and higher-boiling components relative to the azeotrope of MEG and DETA have been removed.

The mixture comprising MEG and DETA may be obtained particularly advantageously from a process for preparing ethyleneamines and ethanolamines by hydrogenating amination of MEG and ammonia in the presence of a heterogeneous catalyst, a catalyst being used whose active composition comprises ruthenium and cobalt but no further metal of group VIII and no metal of group Ib, and is present as a shaped catalyst body which has a diameter of <3 mm in each case in sphere form or extrudate form, a height of <3 mm in tablet form and in each case an equivalent diameter L=1/a' of <0.70 mm in the case of all other geometries, where a' is the external surface area per unit volume ($mm_s^2/mm_p^3$):

$$a' = \frac{Ap}{Vp}$$

where $A_p$ is the external surface area of the shaped catalyst body ($mm_s^2$) and $V_p$ is the volume of the shaped catalyst body ($mm_p^3$).

In particular, in a first separation sequence, first excess ammonia, water formed and any hydrogen present are removed from the product mixture obtained in the hydrogenating amination of MEG and ammonia in the presence of a heterogeneous catalyst for preparing ethyleneamines and ethanolamines. The distillation columns required for this purpose can be designed by the person skilled in the art with methods familiar to him, especially with regard to the number of separating stages, reflux ratios, etc. Ammonia obtained here and/or water obtained are preferably recycled into the reaction.

The reaction mixture of the hydrogenating amination of MEG, from which excess ammonia, water formed and any hydrogen present have preferably been removed in a first separation sequence is subsequently separated in a second separation sequence into unconverted MEG, and also MEOA, EDA, PIP, DETA, AEEA and higher ethyleneamines. In this separation sequence, lower- and higher-boiling components relative to the azeotrope of MEG and DETA are removed first and then the mixture concentrated in MEG and DETA is separated by extractive distillation with TEG as the selective solvent into a stream comprising MEG and a stream comprising DETA.

For this purpose, in particular, the reaction mixture of the hydrogenating amination of MEG, from which excess ammonia, water formed and any hydrogen present have preferably been removed, is separated in a first distillation unit KI into a top stream comprising the ethylenediamine and piperazine components of the reaction mixture and a bottom stream comprising the components of the reaction mixture having a boiling point greater than the boiling point of piperazine, the bottom stream being fed to a second distillation column KII and separated therein into a top stream comprising monoethylene glycol, diethylenetriamine and monoethanolamine, and a bottom stream comprising components having a higher boiling point than monoethylene glycol and diethylenetriamine, the top stream being fed to an extractive distillation column KIII to which is fed, at the same separating stage or height, a stream comprising triethylene glycol as a selective solvent for diethylenetriamine, a diethylenetriamine-laden stream comprising the selective solvent triethylene glycol being removed via the bottom, and a monoethylene glycol-comprising stream freed substantially of diethylenetriamine being removed via the top in the extractive distillation column KIII.

The bottom stream from the extractive distillation column KIII, comprising selective solvent laden with DETA, is preferably fed to a desorption column KIV and separated therein into a top stream comprising DETA and a bottom stream comprising TEG. The TEG-comprising bottom stream from the extractive distillation column KIV is preferably recycled into the extractive distillation column KIII.

The composition of the stream to be separated in the extractive distillation, i.e. of the feed stream to the extractive distillation column, is preferably from 60 to 90% by weight of MEG, from 1.5 to 6% by weight of DETA, from 10 to 30% by weight of MEOA and less than 1% by weight of piperazine. In this case, MEG and DETA are preferably present in a weight ratio in the range from 18:1 to 42:1.

The extractive distillation with TEG as the selective solvent for DETA is preferably operated in such a way that the proportion by weight of the stream comprising triethylene glycol or of the streams comprising triethylene glycol, based on the weight of the feed stream comprising monoethylene glycol and diethylenetriamine, is in the range from 1.5:1 to 10:1.

The extractive distillation column is preferably designed with a number of from 5 to 50 theoretical plates, in particular from 10 to 30 theoretical plates, more preferably with 20 theoretical plates, and is operated at a temperature in the range from 60 to 200° C., preferably from 100 to 180° C., and a pressure of from 0.01 to 1 bar absolute, preferably from 0.01 to 0.5 bar absolute.

The invention will be illustrated in detail below with reference to a drawing and to a working example.

In the drawing, the sole FIGURE, FIG. 1, shows the scheme of a preferred plant for performing the process according to the invention.

A feed stream 1 comprising MEG and DETA is fed to a first distillation unit KI and separated therein into a top stream 2 comprising especially EDA and PIP, and a bottom stream 3 comprising components having a boiling point greater than the boiling point of PIP. The bottom stream 3 of the first distillation unit KI is fed to a second distillation unit KII, and separated therein into a top stream 4 comprising MEG and DETA, and a bottom stream 5 comprising higher-boiling components compared to MEG and DETA, in particular AEEA, DEOA and higher boilers.

The top stream 4 from the second distillation unit KII is fed to an extractive distillation column KIII to which is fed, at the same separating stage or higher, a stream 6 comprising TEG as the selective solvent for DETA, and separated therein into a bottom stream 8 comprising TEG laden with DETA and a top stream 7 which comprises predominantly MEG and additionally MEOA and is largely free of DETA.

The bottom stream 8 from the extractive distillation column KIII is fed to a desorption column KIV and separated therein into a top stream 10 comprising predominantly DETA and a bottom stream 9 which comprises TEG and which, in the preferred variant shown in the FIGURE, is recycled into the extractive distillation column KIII.

WORKING EXAMPLE

A reactor effluent from the hydrogenating amination of MEG with ammonia in the presence of a heterogeneous catalyst comprises, after removal of ammonia and water, 52% by weight of MEG, 21.5% by weight of MEOA, 17% by weight of EDA, 2% by weight of DETA and 2% by weight of AEEA, 3.5% by weight of piperazine and 2% by weight of higher boilers.

This mixture is fed as feed stream 1 to the first distillation unit KI and separated therein into a top stream 2 comprising EDA and PIP and a bottom stream 3 comprising higher-boiling components compared to PIP. The bottom stream 3 from the first distillation unit KI is fed to a second distillation unit KII and a stream 5 comprising high boilers is removed therein, as is a top stream 4 which is fed as the feed stream in the extractive distillation column KIII. The mass ratio of MEG and DETA in the feed stream 4 is 28. The extractive distillation column KIII is operated at a pressure of 40 mbar and a reflux of 1. It is designed with 20 theoretical plates and the stream 4 comprising MEG and DETA is fed in at about the middle based on the separating stages.

The selective solvent for DETA, stream 6, is added 1 to 2 theoretical plates above the mixture 4 to be separated. The mass flow rate of the stream 6 comprising the selective solvent TEG, at a temperature thereof of 25° C., is 3.8 times that of the stream 4 to be separated. At the top of the extractive distillation column KIII, a stream 7 comprising MEG and MEOA is removed, whose DETA content is less than 10 ppm. At the bottom of the extractive distillation column KIII, a DETA-laden stream of the selective solvent TEG is drawn off, which is virtually MEG-free (MEG content less than 10 ppm). Stream 8 is separated in the desorption column KIV into a DETA comprising top stream 10 and a bottom stream 9 which comprises the selective solvent TEG and which is recycled into the extractive distillation column KIII.

What is claimed is:

1. A process comprising:
    providing a mixture comprising monoethylene glycol and diethylenetriamine; and
    subjecting the mixture to extractive distillation with a diethylenetriamine-selective solvent comprising triethylene glycol to provide a first stream comprising monoethylene glycol and a second stream comprising diethylenetriamine;
    wherein the first stream is substantially free of diethylenetriamine, and wherein the second stream is substantially free of monoethylene glycol.

2. The process according to claim 1, wherein diethylenetriamine is present in the first stream in an amount of less than 5% by weight, and wherein monoethylene glycol is present in the second stream in an amount of less than 2% by weight.

3. The process according to claim 1, wherein diethylenetriamine is present in the first stream in an amount of less than 0.1% by weight, and wherein monoethylene glycol is present in the second stream in an amount of less than 0.1% by weight.

4. The process according to claim 1, wherein diethylenetriamine is present in the first stream in an amount of less than 10 ppm, and wherein monoethylene glycol is present in the second stream in an amount of less than 10 ppm.

5. The process according to claim 1, wherein the mixture comprises a reaction mixture from a hydrogenating amination process of monoethylene glycol with ammonia in the presence of a heterogeneous catalyst, wherein components having lower- and higher-boiling points relative to the azeotrope of monoethylene glycol and diethylenetriamine have been removed from the reaction mixture prior to subjecting to the reaction mixture to extractive distillation.

6. The process according to claim 1, wherein the mixture comprises a reaction mixture from a hydrogenating amination process of monoethylene glycol with ammonia in the presence of a heterogeneous catalyst,
    wherein the reaction mixture is fed to a first distillation unit and the reaction mixture is separated in the first distillation unit to form a top stream comprising ethylenediamine and piperazine components from the reaction mixture and a bottom stream comprising components from the reaction mixture having a boiling point greater than the boiling point of piperazine,
    feeding the bottom stream to a second distillation unit and separating the bottom stream in the second distillation unit to form a second top stream comprising monoethylene glycol, diethylenetriamine and monoethanolamine, and a second bottom stream comprising components having a higher boiling point than monoethylene glycol and diethylenetriamine, and
    wherein subjecting the mixture to extractive distillation comprises feeding the second top stream to an extractive distillation unit and feeding to the extractive distillation unit at the same separating stage or height, a stream comprising the diethylenetriamine-selective solvent comprising triethylene glycol, and removing a diethylenetriamine-laden stream comprising the triethylene glycol from a bottom of the extractive distillation unit, and removing a monoethylene glycol-comprising stream substantially free of diethylenetriamine from a top of the extractive distillation unit.

7. The process according to claim 6, wherein the diethylenetriamine-laden stream comprising the triethylene glycol removed from the bottom of the extractive distillation unit is fed to a desorption column and separated therein into a top stream comprising diethylenetriamine and a bottom stream comprising triethylene glycol.

8. The process according to claim 7, wherein the bottom stream from the desorption column is recycled into the extractive distillation unit.

9. The process according to claim 6, wherein the second top stream comprises monoethylene glycol and diethylenetriamine in a weight ratio of 18:1 to 42:1.

10. The process according to claim 6, wherein the second top stream comprises 60 to 90% by weight of monoethylene glycol, 1.5 to 6% by weight of diethylenetriamine, 10 to 30% by weight of monoethanolamine and less than 1% by weight of piperazine.

11. The process according to claim 6, wherein the proportion by weight of the stream comprising triethylene glycol, based on the weight of the second top stream comprising monoethylene glycol and diethylenetriamine, is 1.5:1 to 10:1.

12. The process according to claim 6, wherein the extractive distillation unit is operated at a temperature of 60 to 200° C. and a pressure of 0.01 to 1 bar absolute and has a number of theoretical plates of 5 to 50.

13. The process according to claim 6, wherein the extractive distillation unit is operated at a temperature of 100 to 180° C. and a pressure of 0.01 to 0.5 bar absolute and has a number of theoretical plates of 10 to 30.

* * * * *